United States Patent
Fava

(10) Patent No.: US 12,376,994 B2
(45) Date of Patent: Aug. 5, 2025

(54) BODY MOUNTED LASER INDIRECT OPHTHALMOSCOPE (LIO) SYSTEM

(71) Applicant: Norlase ApS, Ballerup (DK)

(72) Inventor: Greg Fava, Redwood City, CA (US)

(73) Assignee: Norlase ApS, Ballerup (DK)

(*) Notice: Subject to any disclaimer, the term of this patent is extended or adjusted under 35 U.S.C. 154(b) by 0 days.

(21) Appl. No.: 17/704,069

(22) Filed: Mar. 25, 2022

(65) Prior Publication Data

US 2022/0211264 A1    Jul. 7, 2022

Related U.S. Application Data

(62) Division of application No. 16/361,768, filed on Mar. 22, 2019.

(Continued)

(51) Int. Cl.
*A61B 3/00* (2006.01)
*A61B 3/12* (2006.01)
(Continued)

(52) U.S. Cl.
CPC ........ *A61F 9/00821* (2013.01); *A61B 3/0033* (2013.01); *A61B 3/12* (2013.01);
(Continued)

(58) Field of Classification Search
CPC .......... A61B 3/00; A61B 3/0033; A61B 3/10; A61B 3/12; A61B 3/14; A61B 3/18;
(Continued)

(56) References Cited

U.S. PATENT DOCUMENTS

2004/0000733 A1    1/2004    Swab et al.
2007/0129775 A1*    6/2007    Mordaunt ........... A61F 9/00821
                                                               606/4

(Continued)

FOREIGN PATENT DOCUMENTS

WO    WO 2014/049132    4/2014

OTHER PUBLICATIONS

Kaustubh et al: "An Improvement on Binocular Indirect Ophthalmoscopy for Diabetic Retinopathy", 2017 Progress In Electromagnetics Research Symposium—Fall (PIERS—FALL), Singapore; Nov. 19, 2017, p. 1807-1815. (Year: 2017).*

(Continued)

*Primary Examiner* — Jie Lei
(74) *Attorney, Agent, or Firm* — ICE MILLER LLP; Justin D. Swindells

(57) ABSTRACT

A body-mounted laser-indirect ophthalmoscope (LIO) system for delivering laser energy into an eye of a patient includes a wearable assembly which secures a control module, laser module, and/or power module (including a battery) to the body of the user. The control module receives activation signals and parameter information from an activation unit a mobile computing device and controls the laser energy emitted by the laser module based on the parameter information. The parameter information is user-provided via a graphical user interface or by voice control (e.g. recognizing voice commands in audio data captured by the mobile computing device). In the preferred embodiment, the wearable assembly includes only a headset, in which case the control, power and laser modules are provided on the headset; however, an alternative embodiment includes a utility belt from which a fiber optic cable for emitting the laser energy is routed to the headset.

15 Claims, 11 Drawing Sheets

Related U.S. Application Data

(60) Provisional application No. 62/646,715, filed on Mar. 22, 2018.

(51) Int. Cl.
    *A61B 90/53* (2016.01)
    *A61F 9/008* (2006.01)
    *G06F 3/16* (2006.01)
    *G10L 15/22* (2006.01)
    *H02J 7/00* (2006.01)
    *A61B 17/00* (2006.01)
    *A61B 90/50* (2016.01)

(52) U.S. Cl.
    CPC .............. *A61B 90/53* (2016.02); *A61F 9/008* (2013.01); *G06F 3/167* (2013.01); *G10L 15/22* (2013.01); *H02J 7/0047* (2013.01); *A61B 2017/00203* (2013.01); *A61B 2017/00221* (2013.01); *A61B 2017/00734* (2013.01); *A61B 2017/00973* (2013.01); *A61B 2090/502* (2016.02); *A61F 2009/00863* (2013.01); *H02J 7/0048* (2020.01)

(58) Field of Classification Search
    CPC ..... A61B 3/02; A61B 90/53; A61B 2009/502; A61B 2017/00203; A61B 2017/00221; A61B 2017/00973; A61B 2017/00734; A61F 9/008; A61F 2009/00863; G10L 15/22; H02J 7/027; H02J 7/0021; G06F 3/16; G06F 3/167

USPC ....... 351/205, 206, 200, 246, 221, 216–218; 606/4, 5

See application file for complete search history.

(56) References Cited

U.S. PATENT DOCUMENTS

| | | |
|---|---|---|
| 2011/0085138 A1 | 4/2011 | Filar |
| 2014/0253867 A1* | 9/2014 | Jiang ..................... G02C 11/10 351/158 |
| 2015/0290031 A1* | 10/2015 | Wellhoefer ............... G06F 3/03 345/156 |
| 2015/0366713 A1 | 12/2015 | Shazly et al. |
| 2015/0366716 A1 | 12/2015 | Clifford et al. |
| 2018/0220889 A1 | 8/2018 | Dirghangi et al. |

OTHER PUBLICATIONS

Fox Ophthalmology Laser—Laser Innovation, 1-4 (2018).
Search Report of the Danish Patent and Trademark Office, mailed on Oct. 30, 2018, from Danish Application No. PA 2018 70238, filed Mar. 2018. 7 pages.
Novack, R., "The Evolution of Laser Technology for Retinal Applications," Retina Today, 43-45 (2009).

\* cited by examiner

BODY MOUNTED LASER INDIRECT OPHTHALMOSCOPE (LIO) SYSTEM

RELATED APPLICATIONS

This application is a Divisional of U.S. patent application Ser. No. 16/361,768, filed on Mar. 22, 2019, which claims the benefit under 35 USC 119(e) of U.S. Provisional Application No. 62/646,715, filed on Mar. 22, 2018, both of which are incorporated herein by reference in their entirety.

BACKGROUND OF THE INVENTION

Ophthalmologists are medical specialists dealing with diagnosing and treating the eyes of patients. Some of these treatments involve delivering laser energy to the patient's eye. In these treatments, doctors regularly set and update parameters for the laser energy to be delivered. These parameters can include power, exposure duration, repeat interval, among other examples.

Commonly, slit lamps are used for delivering the laser energy to the patient's eye. In these systems, the patients sit up in an examination chair, rest their chin on a chin rest, and place their forehead against a forehead band, both of which keep the patient's head in place during the procedure. However, some patients are unable to sit at a slit lamp due to the patient's age, size, or health condition, among other factors.

A Laser Indirect Ophthalmoscope (LIO), is a head mounted device, worn by the doctor to deliver laser energy into a patient's eye. Current systems use a laser console for generating the laser light and a long fiber optic coupled to the LIO for delivering the laser light to tissue. The laser console includes a laser source of multiple lasing mediums and wavelengths, a power source (for example, providing AC/DC conversion), laser drive and parameter control systems, and a user interface. The user interface comprises physical knobs and switches or a touchscreen and can be part of the laser console itself or a remote control device that communicates with the laser console. Activation devices (e.g. footswitches) connect to the laser consoles and activate the laser emission, for example, by sending an activation signal to the laser console in response to engagement of an activation mechanism (e.g. compression of the footswitch). Input voltage for these systems is generally 90-240 VAC.

During procedures using the LIO, the doctor moves the laser console, which is positioned on a cart or table, to be in the proximity of the patient who is usually in a supine position. The doctor then walks around the patient to deliver the laser energy to the desired portions of the retina. If a parameter change is needed, the doctor physically returns to the laser console to make the change or has an assistant, for example, standing next to the laser console, make the change.

SUMMARY OF THE INVENTION

One of the biggest limitations with LIO systems is doctor mobility. Currently, LIO systems are tethered, via fiber optic cable, to the laser console somewhere near the patient, and the laser consoles also need to be positioned near an electrical outlet. Whenever a parameter change is needed, the doctor must return to the laser console, make the change, and then return to the patient to continue the procedure, requiring additional time for the doctor to reorient after making the change. This sequence also forces the doctor to reroute the fiber optic cable during the portions of the procedure requiring mobility to and from the laser console. One potential solution to this problem has involved verbally giving parameter changes to an assistant located near the laser console. However, this solution is more costly, as more health care personnel are needed for each LIO procedure.

Another limitation of LIO systems is the fiber optic cable connecting the laser console to the headset. Portions of these cables, which can be 15 feet long for example, often end up draped across the patient's body and/or on the floor. Because the fiber optic cables are so exposed and can break easily during routine use, accidental damage is common, and they require frequent service and repair.

A body-mounted LIO system according to the current invention provides greater mobility and freedom to doctors during procedures, increases efficiency, and minimizes exposure of the fiber optic cable to traumatic events that may cause it to break. More specifically, the present system includes a wearable assembly such as a headset, a utility belt, and/or a backpack which includes many of the components that would be part of the laser console in previous systems, such as the laser, power source and control module. This increases mobility for the doctor who is no longer tethered to the laser console by the fiber optic cable. The fiber optic cable can be completely unexposed or, for example, routed from a utility belt, up the doctor's back, to the headset, decreasing the probability of incurring costly damage to the LIO fiber.

Additionally, the LIO system provides a wireless portable user computer device, such as a tablet or smartphone, rendering a graphical user interface. That device can be placed next to the patient, allowing the doctor to access and change the parameters while staying focused on the patient. The user interface includes a voice control process for recognizing spoken commands and parameter information. Audible feedback of current and updated parameters is also provided. A graphical user interface (rendered, for example, on a touchscreen display of a mobile computing device) provides an additional means for accessing and changing the parameters. In either case, parameter information is generated and wirelessly sent to the control module of the LIO system e.g. via Bluetooth Low Energy (BLE) protocol wireless data connection.

In one example, the mobile computing device detects a wake word (which is a special phrase to indicate that verbal commands follow). In response to detecting the wake word, the mobile computing device captures audio data, and the voice control process recognizes in the audio data a spoken command (in any multitude of languages) from a predetermined set of commands. Parameter information is then generated based on the audio data, including which commands and other spoken information were recognized by the voice control process.

Additional benefits provided by the current invention include decreased space consumption as a cart or table is no longer required for the laser console. This, combined with the use of batteries rather than an AC power source, increases the range of potential treatment locations, potentially allowing for increased usage in developing countries that may not have electricity required for standard LIO treatment.

According to a preferred embodiment of the current invention, the laser module, battery and control electronics are integrated entirely into the headset of the LIO system. These components are miniaturized and simplified, and thermal management of the laser head is optimized to allow the components to be attached as part of the headband or ocular head and placed to allow proper weight balancing of the whole LIO assembly. A high capacity battery powers both the white light illumination of the headset and the laser. This embodiment limits the number of separate system components to three (the headset, the activation unit, and the mobile computing device providing the user interface), thus maximizing system mobility.

According to another embodiment, the laser module, battery and control electronics are integrated into a utility belt. The fiber optic cable, from which the laser energy is emitted, is routed from the utility belt to the headset, which also includes the binocular indirect ophthalmoscope.

In general, according to one aspect, the invention features a laser indirect ophthalmoscope system for delivering laser energy to an eye of a patient. The system comprises a mobile computing device, a voice control process, and a control module. The mobile computing device captures audio data. The voice control process, in turn, receives the audio data and generates parameter information based on the captured audio data. The control module receives the parameter information and sets the parameters for the delivered laser energy based on the parameter information.

In embodiments, the voice control process, which, for example, executes on the mobile computing device, generates the parameter information by recognizing spoken language in the captured audio data. The mobile computing device captures the audio data in response to detecting a predetermined wake word and provides audio feedback confirming the parameter information generated by the voice control process. Additionally, the parameter information can also be generated by the mobile computing device based on input received via a graphical user interface rendered on a touchscreen display of the mobile computing device. An activation unit (e.g. a footswitch) sends activation signals for emitting the laser energy to the control module in response to engagement of an activation mechanism of the activation unit (e.g. compression of the footswitch). The parameter information is received by the control module via a wireless communication interface.

In general, according to another aspect, the invention features a laser indirect ophthalmoscope system for delivering laser energy to an eye of a patient. The system comprises a laser module for generating and delivering the laser energy. A wearable assembly secures the laser module to a body of a user of the laser indirect ophthalmoscope system.

In embodiments, the wearable assembly can include a headset worn on the user's head and/or a utility belt worn around the user's waist and can also secure a control module for setting parameters for the delivered energy and a power module for providing power to the laser module to the user's body. The power module comprises a portable battery for providing the power.

In general, according to another aspect, the invention features a method for delivering laser energy to an eye of a patient using a laser indirect ophthalmoscope system. Audio data is captured, and parameter information is generated based on the captured audio data. Parameters for the delivered laser energy are set based on the parameter information.

In general, according to another aspect, the invention features a method for delivering laser energy to an eye of a patient using a laser indirect ophthalmoscope system. A laser module generates and delivers the laser energy. A wearable assembly secures the laser module to a body of a user of the laser indirect ophthalmoscope system.

In general, according to another aspect, the invention features a laser indirect ophthalmoscope system for delivering laser energy to an eye of a patient. The system includes a mobile computing device for generating parameter information and a control module. The control module receives the parameter information via a wireless communication interface and sets parameters for the delivered laser energy based on the parameter information.

In general, according to another aspect, the invention features a laser indirect ophthalmoscope system for delivering laser energy to an eye of a patient. The system includes an activation unit, a mobile computing device, and a control module. The activation unit generates activation signals based on the user input received via an activation mechanism. The mobile computing device receives the activation signals via a wireless communication interface and relaying the activation signals to the control module, which receives the activation signals via a wireless communication interface and generates control signals for the delivered laser energy based on the activation signals.

In general, according to another aspect, the invention features a laser indirect ophthalmoscope system for delivering laser energy to an eye of a patient. The system comprises a laser module for generating and delivering the laser energy and a plurality of interchangeable batteries for providing stored power to the laser module. The predetermined storage capacity for the batteries is based on an estimated amount of power consumed during a single treatment.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Figure 1:
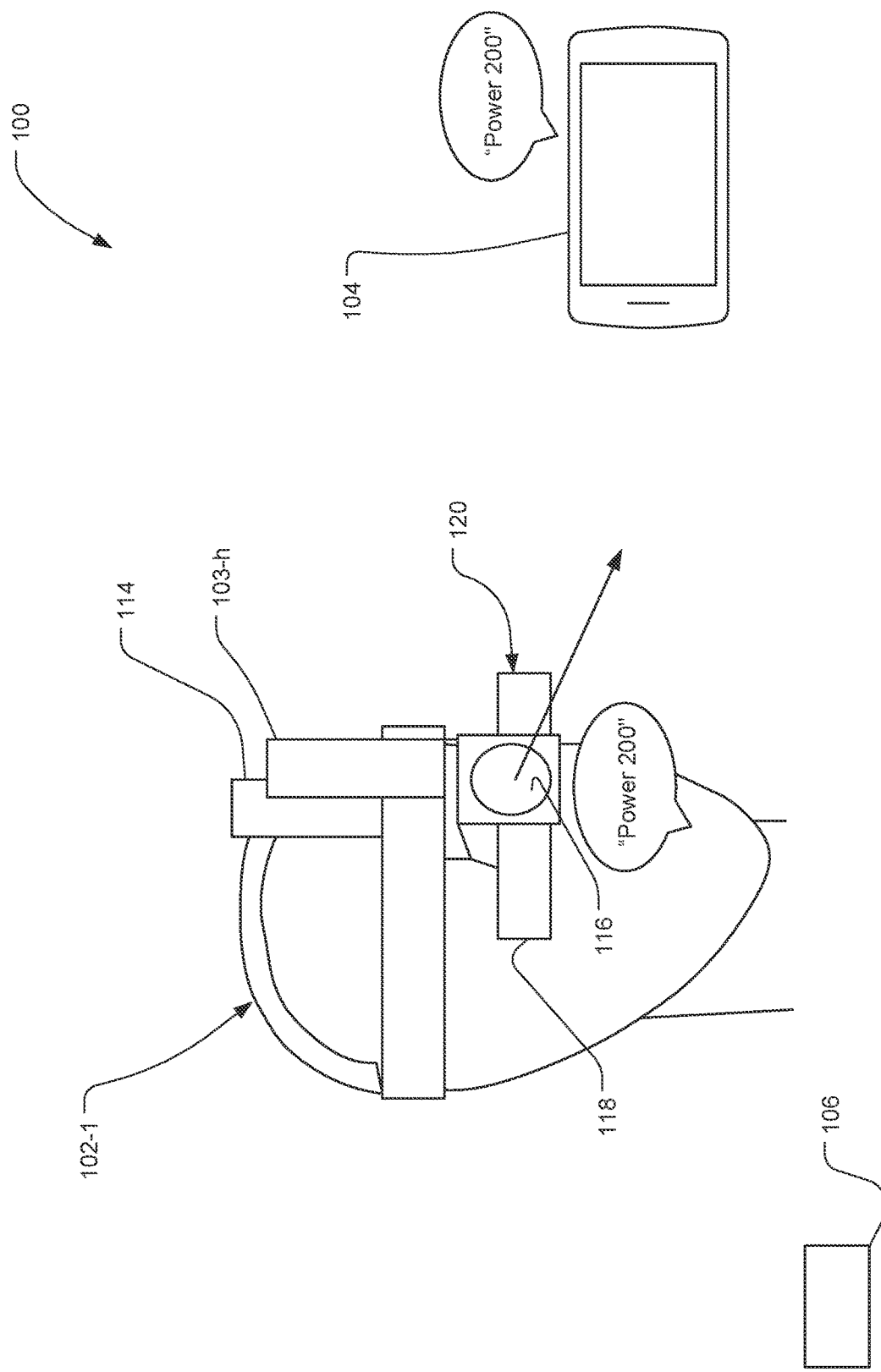
FIG. 1 is an illustration of an exemplary body-mounted laser-indirect ophthalmoscope (LIO) system according to an embodiment of the current invention comprising a headset unit attached to a headset.

FIG. 1 is an illustration of a body-mounted LIO system 100 according to the preferred embodiment of the current invention. In general, the body-mounted LIO system 100 delivers laser energy to an eye of a patient. A user of the LIO system 100 is typically a doctor such as an ophthalmologist.

The body-mounted LIO system 100 includes a binocular indirect ophthalmoscope 120, one or more body-mounted units 103, an activation unit 106, a mobile computing device 104, and one or more wearable assemblies 102.

In general, the body-mounted units 103 include (e.g. electrical) components for delivering the laser energy to the eye of the patient.

The binocular indirect ophthalmoscope 120 is an optical device for examining the inside of the eye of the patient. The binocular indirect ophthalmoscope 120 includes an illumination unit 114 for providing white light and an optical system including a viewing aperture 118 and an exit aperture 116 from which the laser energy is emitted (which is also an entrance aperture for image information e.g. for viewing the patient's eye).

The wearable assembly 102 which secures the body-mounted LIO system 100, including the body-mounted unit(s) 103 and/or the binocular indirect ophthalmoscope 120 to the user's body via one or more wearable objects such as a headset, a utility belt, or a backpack, among other examples.

In the illustrated example, the wearable assembly 102 comprises only a headset 102-1, which is worn on the user's head. The binocular indirect ophthalmoscope 120 is attached to the headset 102-1 and secured to the user's head in a position such that the user's eye is aligned with the viewing aperture 118. The body-mounted unit 103 is a headset unit 103-h, which is attached to the headset 102-1.

In general, the activation unit 106 receives user input and sends activation signals indicating that the laser energy should be emitted.

Preferably, the mobile computing device 120 is a tablet computer such as a commodity user device running IOS or Android operating systems. Alternatively, the mobile computing device 120 could be a smartphone device, laptop computer, or phablet computer (i.e., a mobile device that is typically larger than a smart phone, but smaller than a tablet), to list a few examples. In general, the mobile computing device 104 provides a user interface and generates parameter information indicating the user-provided parameters based on input received via the user interface. In the illustrated example, the user interface is a voice control interface that allows the user to indicate parameter information using verbal commands. In the illustrated example, the user provides a verbal command ("Power 200"), and the mobile computing device 120 provides audible feedback confirming the command.

Figure 2:
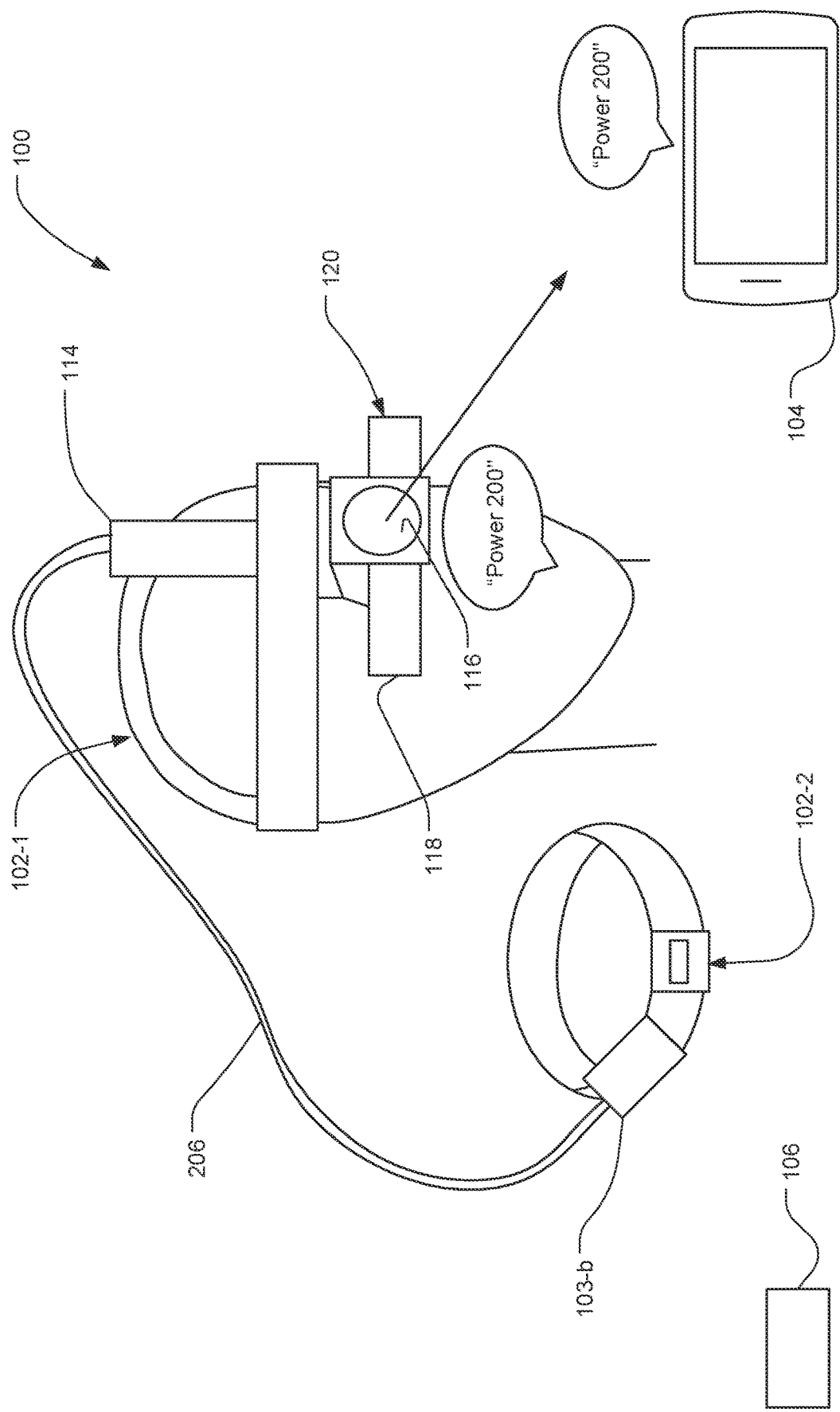
FIG. 2 is an illustration of the body-mounted LIO system according to another embodiment comprising a belt unit attached to a utility belt.

FIG. 2 is an illustration of the body-mounted LIO system 100 according to another embodiment of the invention.

The body-mounted LIO system 100 is similar to the embodiment described with respect to FIG. 1. As before, the headset 102-1 includes the binocular indirect ophthalmoscope 120 and the illumination unit 114.

Now, however, the body-mounted LIO system 100 includes a utility belt 102-2, which is a wearable assembly 102 worn around the user's waist. In the illustrated embodiment, a belt unit 103-b is attached to the utility belt 102-2. The belt unit contains a laser system that generates laser energy. The laser energy is delivered to the illumination unit 114 via a fiber optic cable 206. The illumination unit then directs that laser energy out through the aperture 116.

In general, the fiber optic cable 206 directs the energy from the belt unit 103-b to the exit aperture 116. While the fiber optic cable 206 is concealed in the previous example, here, the fiber optic cable 206 is several feet long (e.g. long enough to connect from the utility belt 102-2 to the headset 102-1 but short enough to remain off of a floor). In the illustrated example, a longer fiber optic cable 206 is routed to the headset 102-1. In practice, this fiber optic cable 206 would be routed up the back of the user such that it is significantly shorter than previous systems and secured in a location where accidental damage is less likely.

Figure 3:
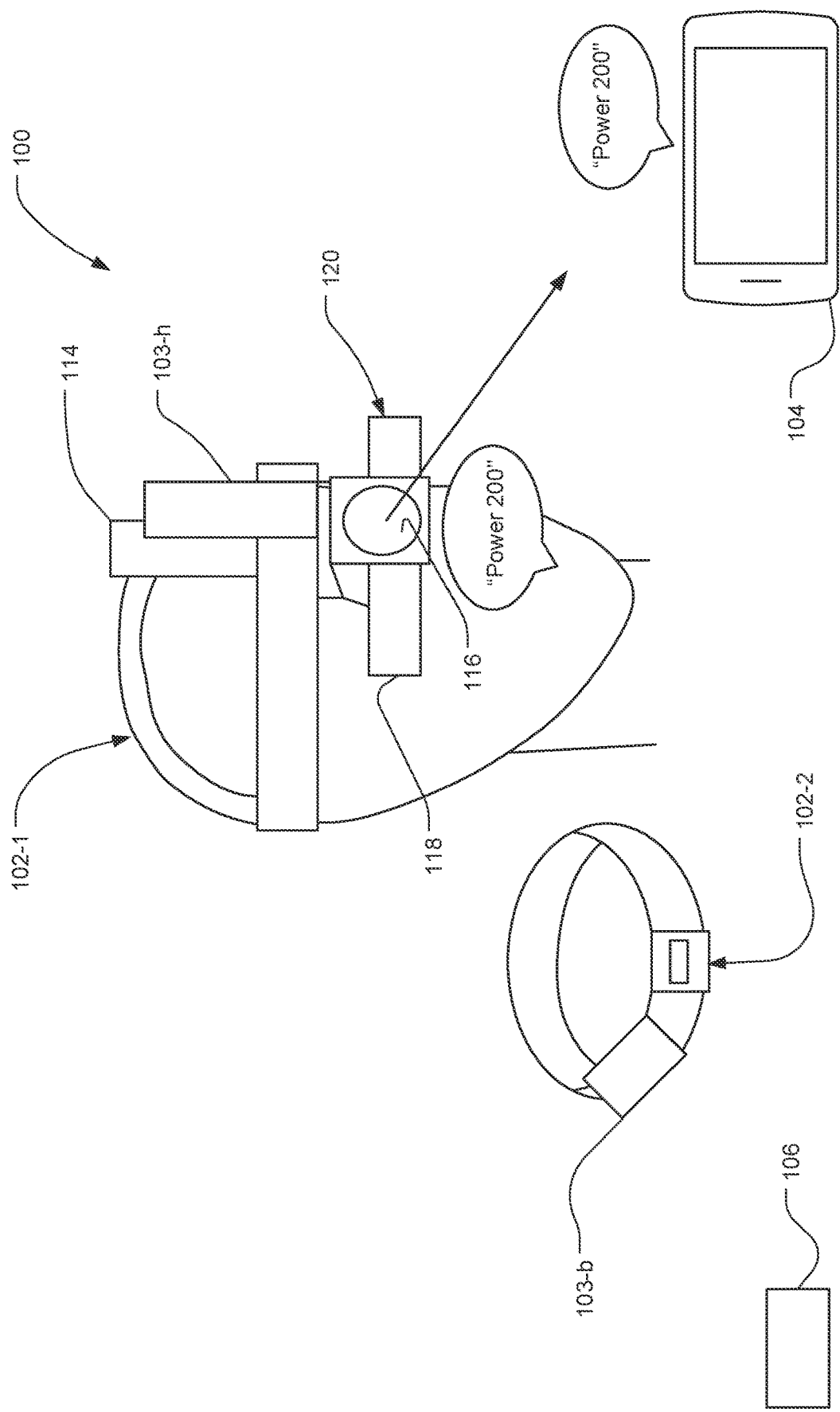
FIG. 3 is an illustration of the body-mounted LIO system according to another embodiment comprising both the headset unit and the belt unit.

FIG. 3 is an illustration of the body-mounted LIO system 100 according to another embodiment of the invention.

The body-mounted LIO system 100 is similar to the embodiments described with respect to FIG. 2.

Now, however, the headset 102-1 includes a headset unit 103-h, and the utility belt 102-2 includes a belt unit 103-b, and the components for delivering the laser energy to the patient's eye are divided between the two body-mounted units 103.

Figure 4:
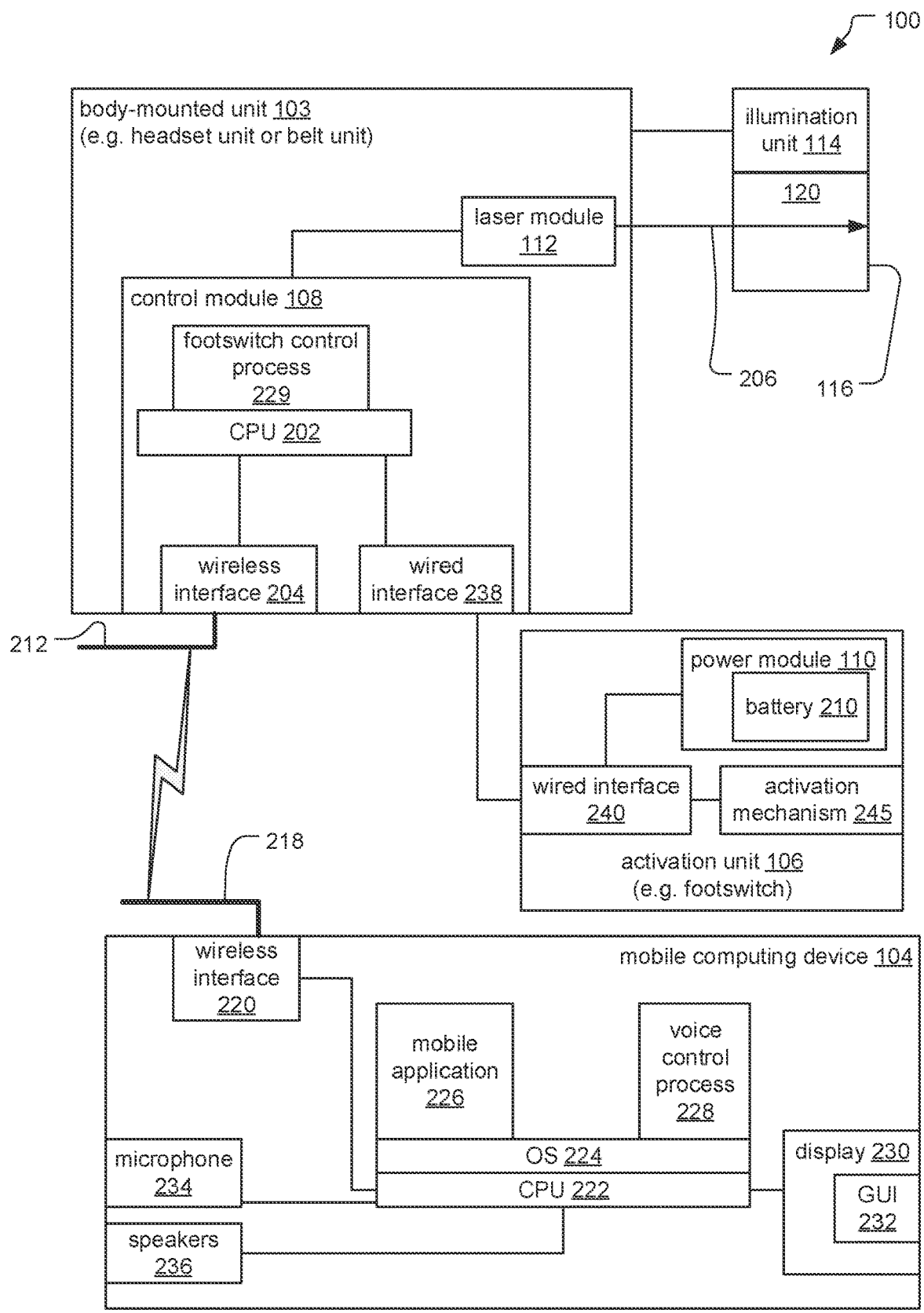
FIG. 4 is a schematic diagram of the body-mounted LIO system according to an embodiment in which a power module housed by an activation unit provides power to a body-mounted unit of the body-mounted LIO system via a wired connection.

FIG. 4 is a schematic diagram of the body-mounted LIO system 100 according to one embodiment, showing the components of the system in more detail.

Internal components of the body-mounted units 103, the activation unit 106, and the mobile computing device 104 are shown. These components, among others, include a control module 108, a laser module 112, and a power module 110.

The power module 110 includes a battery 210, which supplies the power provided to the control module 108, laser module 112, illumination unit 114 and/or the activation unit 106. Among other functions, the power module 110 performs the functions of a battery management system (e.g. preventing the battery from operating outside its Safe Operating Area, monitoring its state, etc.).

The laser module 112 includes one or more lasers, preferably semiconductor lasers. The module produces and emits the laser energy according to certain user-provided parameters such as power, exposure duration, and repeat interval, among other examples. The laser module 112 includes a fiber optic cable 206 for emitting the laser energy. The fiber optic cable 206 is routed through the binocular indirect ophthalmoscope 120 such that the laser energy is emitted from the exit aperture 116.

The control module 108 controls the laser energy delivered by the laser module 112 based on information and/or signals received from the mobile computing device 104 and/or the activation unit 106, including parameter information, connection status information pertaining to communication links between components of the body-mounted LIO system 100, control signals, and/or activation status information indicating an activation status of the activation unit 106. In response to receiving the parameter information, the control module 108 sets the parameters for the laser energy. In response to receiving activation signals, the control module 108 sends control signals reflecting the user-provided parameters to the laser module 112 activating the laser module and causing it to produce and/or emit the laser energy. The control module 108 includes a central processing unit (CPU) 202 such as a microcontroller with integrated memory, a wireless interface 204, which includes antennas, and/or a wired interface 238, which includes a wired jack such as a USB-C port. The CPU 202 directs the functionality of the control module 108 such as receiving parameter information and/or activation signals via the wireless interface 204 and antenna 212 and/or the wired interface 238, as well as sending control signals to the laser module 112.

Executing on the CPU 202 of the control module 108 (or possibly the CPU 222 of the mobile computing device 104) is a footswitch control process 229, which, in general, directs the communication between the control module 108 and/or mobile computing device 104 and the activation unit 106, for example, by monitoring the connection and terminating laser delivery in certain situations.

The footswitch control process 229 provides important safety features pertaining to the use of the activation unit 106. Namely, the footswitch control process 229 optimizes the response time between the activation unit 106 and the delivery of laser energy by the laser module 112 and prevents delivery of laser energy 112 in a situation in which an activation status (e.g. depression or release of a foot pedal of the activation unit 106) is unknown or inaccessible. More specifically, the footswitch control process 229 monitors for a consistent and sufficiently strong wired and/or wireless communication link between the activation unit 106 and the control module 108 or mobile computing device 104 and sends connection status information and/or control signals to the control module 108 based on the status of the wired and/or wireless communication link.

In one example, the footswitch control process 229 continually polls the activation unit 106 by sending a query message to the activation unit 106 in response to which the activation unit 106 sends a response (ACK) message back to the footswitch control process 229. In response to determining that the connection was disrupted based on a predetermined threshold (e.g. a response message was not received within a predetermined period of time), the footswitch control process 229 immediately sends the connection status information and/or the control signals to the control module 108 indicating that the connection between the activation unit 106 and the footswitch control process 229 was lost and that the laser module 112 should terminate emitting laser energy.

In one example, the predetermined threshold for determining whether the wireless communication link was lost is a value corresponding to a duration of time elapsed since sending the most recent query message. The threshold is set sufficiently low so as to minimize delays between activation/release of the activation unit 106, or detection of the disrupted communication link, and delivery or termination of the laser energy.

In another example, the footswitch control process 229 polls the activation unit 106 with a frequency based on a predetermined polling interval. The polling interval is a value representing a duration of time between transmission of each query message, or a value representing a quantity of query messages sent per unit of time, among other examples. As with the above described threshold, the value of the polling interval is set sufficiently low so as to minimize delays response time delays between the activation unit 106 and the control module 108.

The footswitch control process 229 is also configured such that messages pertaining to the activation status of the activation unit 106 are prioritized and/or escalated with respect to other communication between the local device with respect to the footswitch control process 229 and other devices and/or with respect to some local computing functions. For example, the footswitch control process 229 overrides routine operations such as transmission of parameter information to the control module 108 and/or processing of voice commands by the voice control process 228 in response to receiving activation signals from the activation unit 106, causing the activation signals to be relayed to the control module 108 before the parameter information is transmitted and before the voice commands are processed by the voice control process 228. In another example, the footswitch control process 229 overrides the routine operations in response to polling the activation unit 106 and determining that the wireless communication link has been disrupted, causing the CPU 222 to send control signals and/or connection status information to the control module 108 before performing the routine operations.

In another example, the control module 108 stops the laser module 112 (e.g. via sending or terminating control signals) from emitting laser energy in response to receiving connection status information from the footswitch control process 229 indicating that the wired and/or wireless communication link between the activation unit 106 and the mobile computing device 104 was disrupted and/or in response to receiving control signals directly from the mobile computing device 104.

In another example, the control module 108 polls the mobile computing device 104 and stops the laser module 112 in response to determining that the wireless communication link between the control module 108 and the mobile computing device 104 was disrupted, based, for example, on determining that an amount of elapsed time since receiving a communication from the mobile computing device 104 exceeds the predetermined threshold.

In general, the activation unit 106 receives user input via an activation mechanism 245 (e.g. a switch or button) and in response to the user input, the activation unit 106 generates and sends activation signals to the control module 108 and/or to the mobile computing device 104, based on the configuration of the body-mounted LIO system 100, via a communication interface. In the preferred embodiment, the activation unit 106 is a footswitch, and engagement with the activation mechanism 245 includes compression of the footswitch by the user's foot, for example. In different examples, the activation unit 106 also houses the power module 110 and/or the control module 108.

The mobile computing device 104 includes a CPU 222, a touchscreen display 230, a wireless interface 222 and antenna 218, a microphone 234 and speakers 236.

The CPU 222 executes firmware/operating system instructions and sends instructions and data to and receives data from the wireless interface 220, the microphone 234, the speakers 236, and the display 230. Executing on typically an operating system (OS) 224 of the CPU 222 are a mobile application 226 and a voice control process 228. The mobile application 226 renders a graphical user interface (GUI) 232 on the touchscreen display 230. The GUI 232 displays and receives information such as input indicating parameter information, for example, by detecting contact between the user and the touchscreen display 230 in certain regions of the touchscreen display 230. The mobile application 226 generates the parameter information based on the input received via the GUI 232 and/or a voice control interface and sends the parameter information to the control module 108 via the wireless interface 220 and antenna 218. The mobile application 226 also performs functions related to configuring the LIO system 100 such as pairing the mobile computing device 104 with the control module 108 and/or setting a wake word, which is a selected phrase for indicating that verbal commands follow.

The microphone 234 captures sound including the wake word and voice commands indicating parameter information provided by the user, which the mobile computing device 104 converts to audio data.

The voice control process 228 generates parameter information based on the captured audio data. In one example, the voice control process 228 recognizes spoken language in the audio data and translates the spoken language to parameter information.

The speakers 236 provide audible feedback confirming the parameter information by producing sound indicating the parameter information generated by the voice control process 228 based on the audio data.

The voice control process 228 and the GUI 232 rendered on the touchscreen display 230 provide a general user interface (UI) for the LIO system 100. In embodiments, the UI for the LIO system 100 also includes physical input mechanisms such as knobs or buttons, which are part of the mobile computing device 104 itself and/or part of peripheral devices connected to the mobile computing device 104 via the wireless interface 220 and/or a physical interface (e.g. data port). In general, the parameter information is generated by the mobile computing device 104 based on any user engagement with the mobile computing device 104 and/or peripheral devices.

The wireless network interface 220 facilitates sending the parameter information, connection status information, control signals, and/or activation signals to the control module 108 via the antenna 218 through a wireless communication link with the control module 108 according to wireless personal area network (WPAN) or wireless local area network (WLAN) protocols such as Bluetooth Low Energy (BLE) or WiFi, among other examples.

In different embodiments and/or configurations, the control module 108, laser module 112, and power module 110 can be included in a single body-mounted unit 103, in different housings or the same housing, or the modules can be divided among multiple body-mounted units 103 and/or the activation unit 106.

In the illustrated example, the body-mounted unit 103 (e.g. the headset unit 103-h according to the example of FIG. 1, or the belt unit 103-b according to the example of FIG. 2) includes the control module 108 and the laser module 112, and the activation unit 106 includes the power module 110. The activation unit 106 includes a wired interface 240 through which it sends the activation signals to the control module 108 and through which the power module 110 provides power to the control module 108, the laser module 112 and/or the illumination unit 114.

Figure 5:
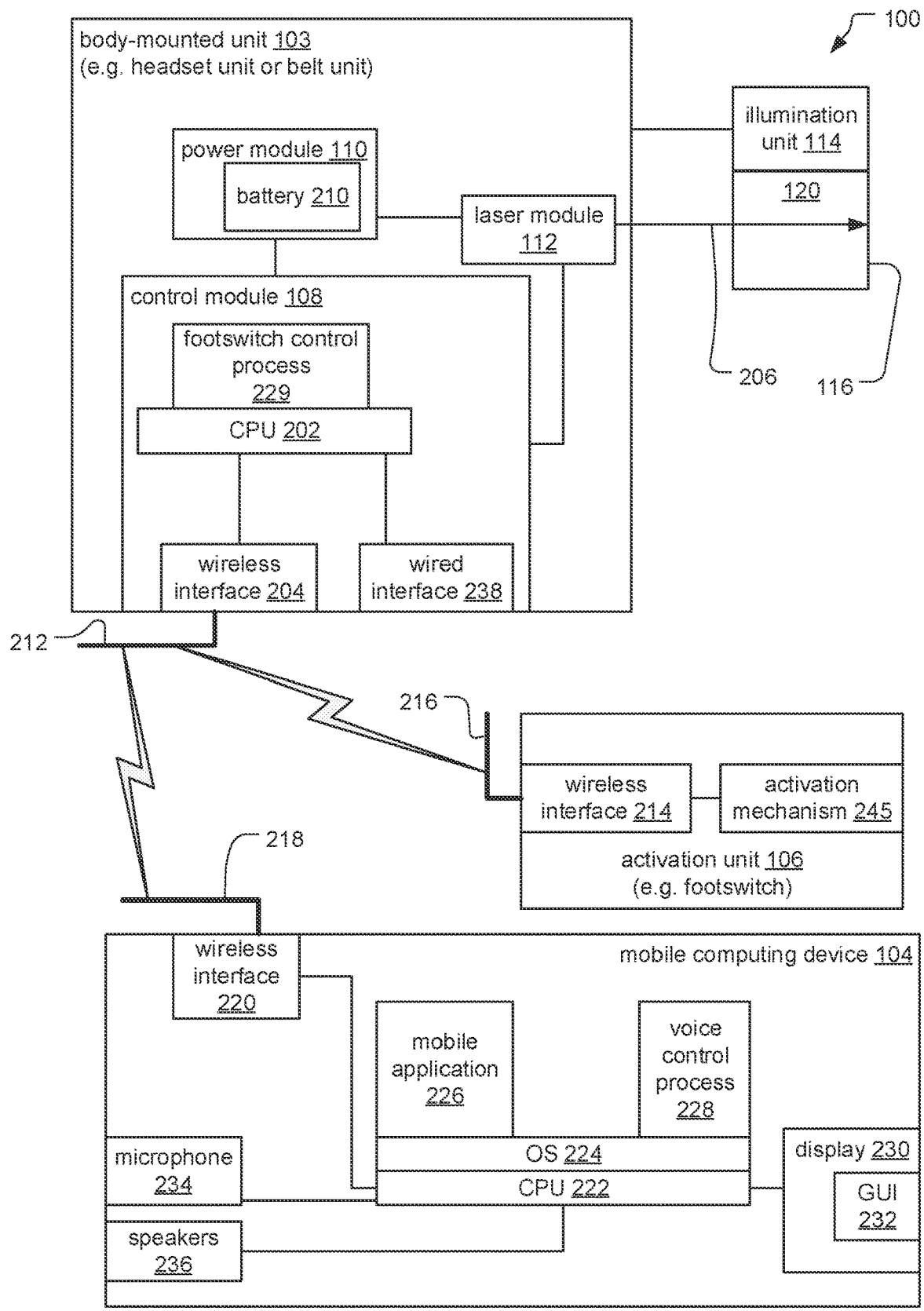
FIG. 5 is a schematic diagram of the body-mounted LIO system according to another embodiment in which the activation unit and a control module communicate directly via a wireless communication link.

FIG. 5 is a schematic diagram of the body-mounted LIO system 100 according to another embodiment of the invention.

The system is similar to that depicted in FIG. 4.

Now, however, the activation unit 106 includes a wireless interface 214 and an antenna 216 through which the activation signals are sent by the activation unit 106 to the control module 108. The wireless interface 214 of the activation unit 106 sends and receives wireless signals to and from the control module 108 (or other wireless-enabled devices) according to wireless personal area network (WPAN) or wireless local area network (WLAN) protocols such as Bluetooth Low Energy (BLE) or WiFi, among other examples.

The body-mounted unit 103 now includes the power module 110, which provides the power from the battery 210 directly to the control module 108, laser module 112 and/or illumination unit 114.

Figure 6:
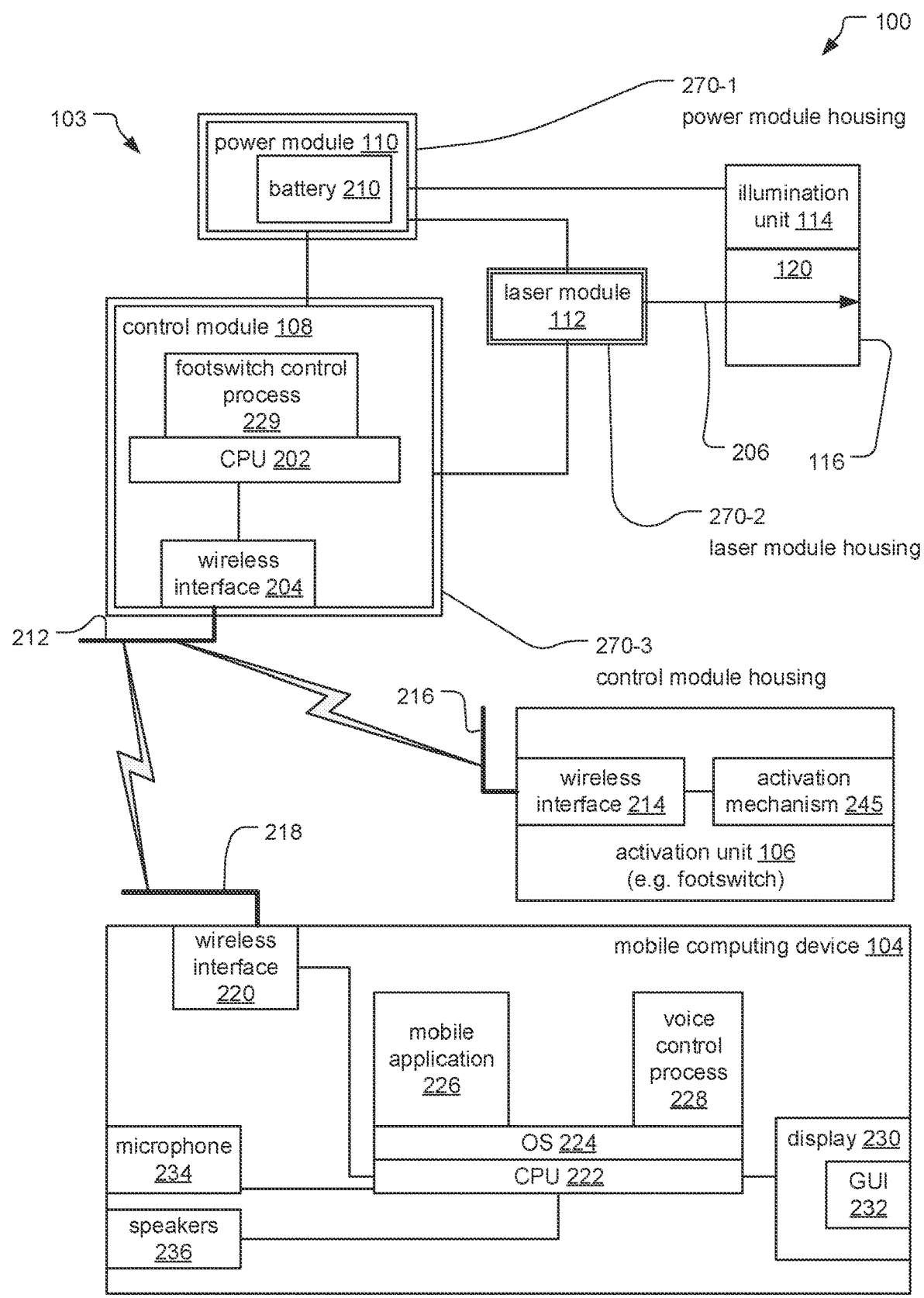
FIG. 6 is a schematic diagram of the body-mounted LIO system according to another embodiment in which the control module, power module, and laser module of the body-mounted unit are housed in separate housings.

FIG. 6 is a schematic diagram of the body-mounted LIO system 100 according to another embodiment of the invention.

The system is similar to that depicted in FIG. 5.

Now, however, each of the control module 108, laser module 112 and power module 110 include separate housings 270, which, in embodiments, are attached to the wearable assembly 102 and/or to each other.

Figure 7:
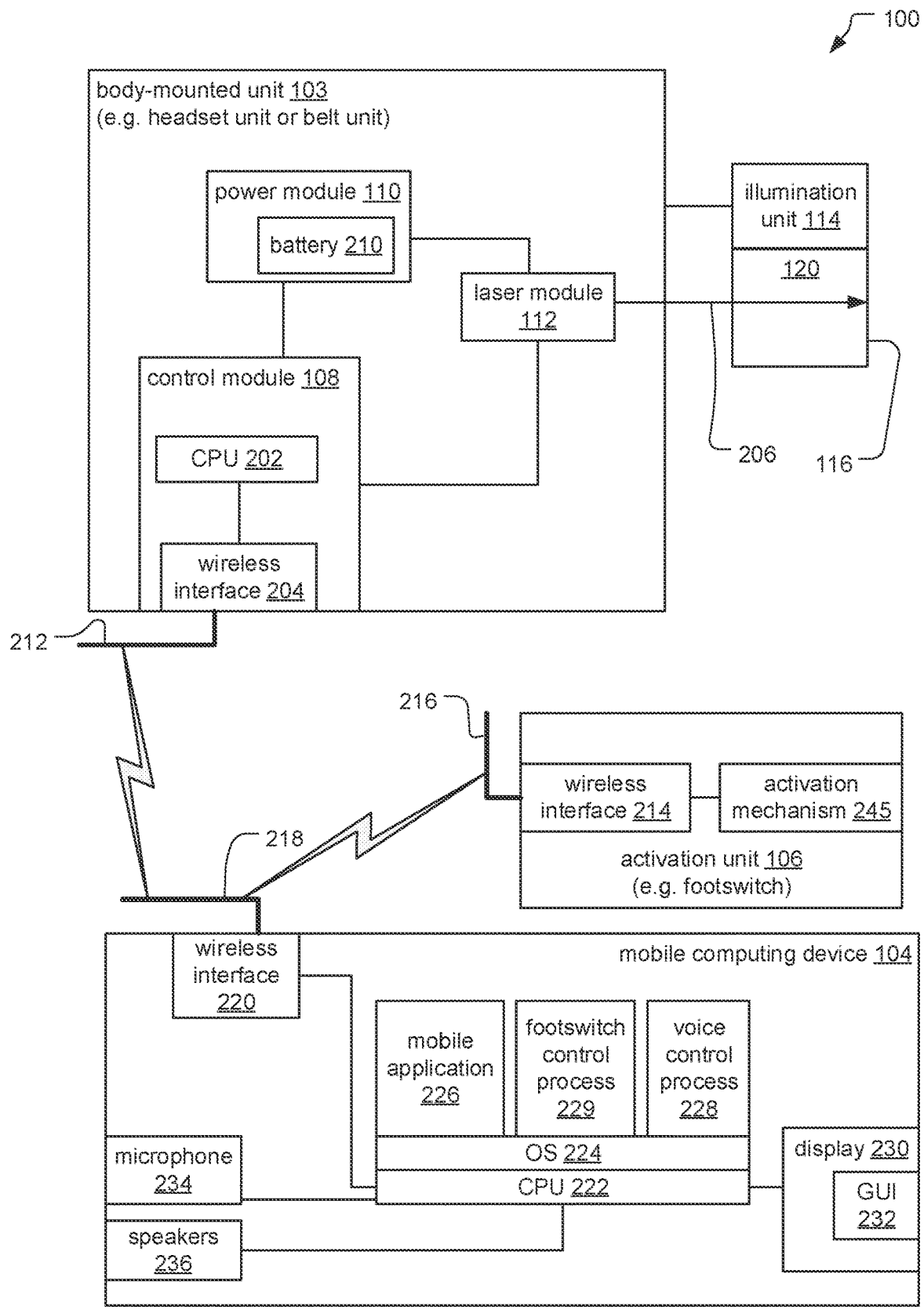
FIG. 7 is a schematic diagram of the body-mounted LIO system according to another embodiment in which the activation unit communicates with a mobile computing device via a wireless communication link.

FIG. 7 is a schematic diagram of the body-mounted LIO system 100 according to another embodiment of the invention.

The system is similar to that depicted in FIG. 5.

Now, however, the activation unit 106 sends the activation signals to the mobile computing device 104 via a wireless communication link between the wireless interface 214 and antenna 216 of the activation unit 106 and the wireless interface 220 and antenna 218 of the mobile computing device 104.

The footswitch control process 229 executes on the CPU 222 of the mobile computing device 104, monitoring the wireless connection between the activation unit 106 and the mobile computing device 104 as previously described. Additionally, in the illustrated embodiment, the footswitch control process 229 relays the activation signals from the activation unit 106 to the control module 108 via the wireless interface 220. In this way, the footswitch control process 229 enables use of a wireless activation unit 106 without requiring dedicated circuitry in the control module 108 for communicating with both the activation unit 106 and the mobile computing device 104.

In this embodiment, the control module 108 also performs the previously described safety functions pertaining to the use of the wireless activation unit 106 as well as the wireless communication link with the mobile computing device 104. For example, the control module 108 stops the laser module 112 (e.g. via sending or terminating control signals) from emitting laser energy in response to determining that the wireless communication link between the control module 108 and the mobile computing device 104 was disrupted and/or in response to receiving activation status information from the mobile computing device 104. The control module 108 determines the connection status information, for example, by polling the mobile computing device 104 based on the polling interval and/or by determining that an amount of elapsed time since receiving a communication from the mobile computing device 104 exceeds the predetermined threshold.

Figure 8:
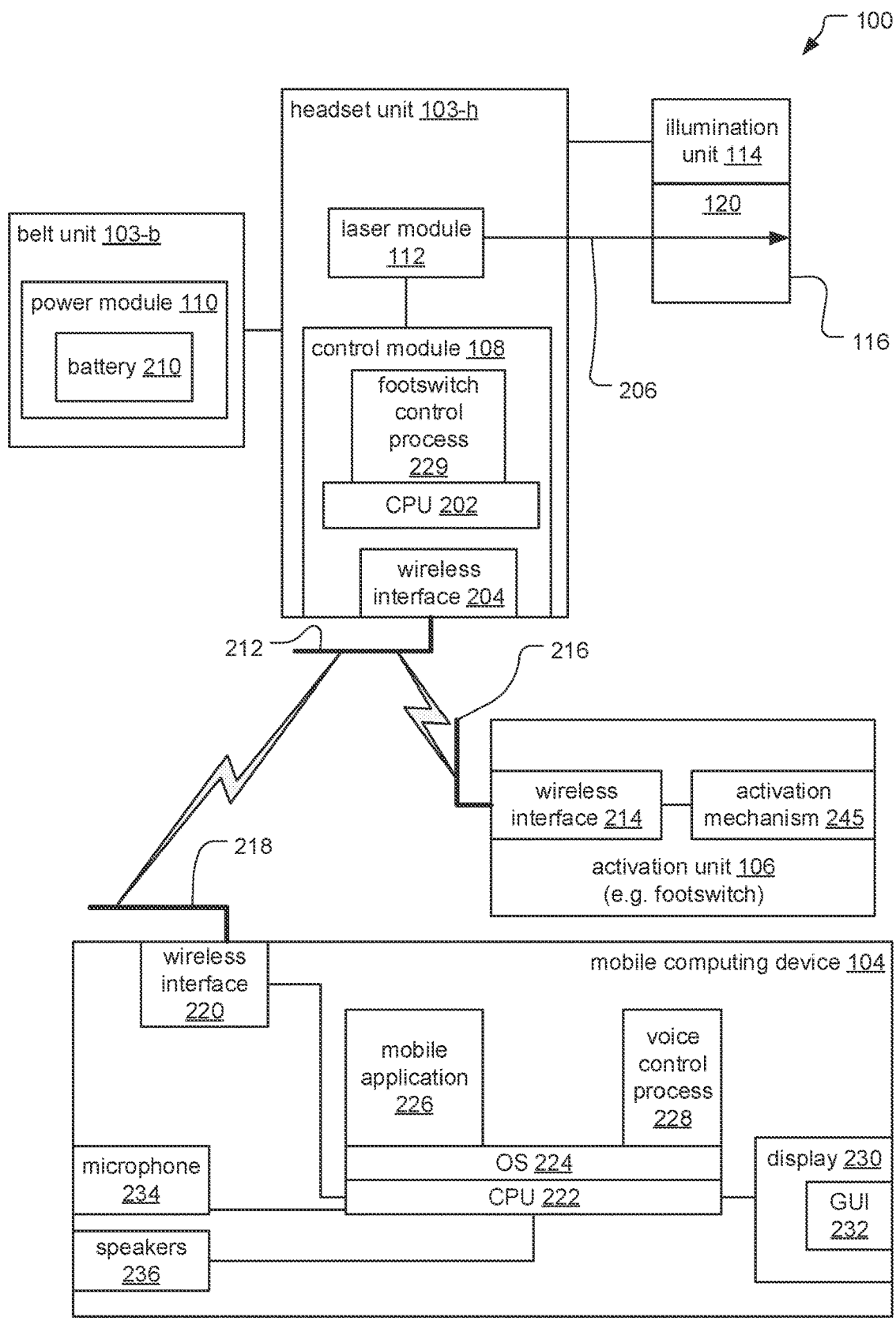
FIG. 8 is a schematic diagram of the body-mounted LIO system according to another embodiment in which the power module is part of the belt unit attached to the utility belt, and the control module and laser module are parts of the headset unit attached to the headset.

FIG. 8 is a schematic diagram of the body-mounted LIO system 100 according to another embodiment of the invention.

The system is similar to that depicted in FIG. 5.

Now, however, the power module 110 is included in the belt unit 103-b rather than the headset unit 103-h, making the headset unit 103-h lighter and thus making the headset 102-1 more comfortable to wear for the user. In general, the power module 110 can be housed in either the belt unit 103-b, the headset unit 103-h, or external to all of the body-mounted units 103, for example, as a component of the activation unit 106.

Figure 9:
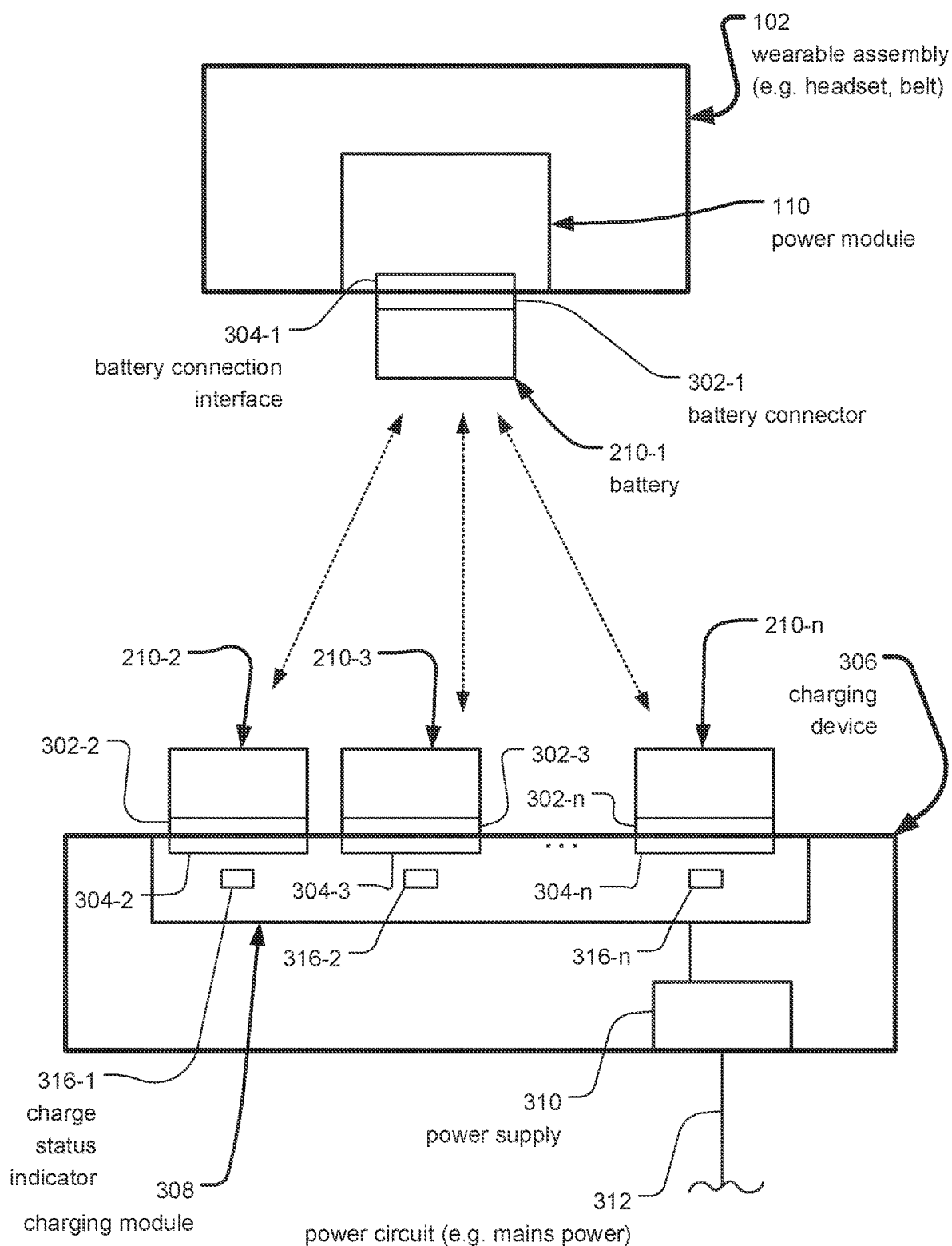
FIG. 9 is a schematic diagram of a power module and batteries of the body-mounted LIO system according to one embodiment.

FIG. 9 is an illustration of the power module 110 and battery 210 according to one embodiment of the invention.

Here, the battery 210 that supplies the power provided to the control module 108, laser module 112 and illumination unit 114 of the wearable assembly 102 is interchangeable with one or more additional batteries 210-2 through 210-n of the LIO system 100.

In one embodiment, each battery 210 has a predetermined capacity, which is based on an amount of power consumed during a predetermined integral number of treatments. For example, the predetermined capacity of the batteries 210 is determined such that each battery 210, when fully charged, stores sufficient power for a single treatment. Limiting the capacity of each battery 210 to that sufficient for one treatment, a lighter and more compact batteries can be used, making the wearable assembly 102 more comfortable for its user.

A charging device 306 of the body-mounted LIO system 100 provides power to be stored by the batteries 210. In the illustrated embodiment, the charging device 306 includes a charging module 308 and a power supply 310.

The power supply 310 converts electric current from a source power circuit 312 (e.g. mains power at 120, 230 or 240 Volts) to an operating voltage, current and frequency to power the charging module 308.

The charging module 308 provides an output current to the batteries 210 via battery connection interfaces 304. In one embodiment, the charging module 308 includes a controller for executing fast and/or smart charging capability, including regulating an output current based on a state of the battery 210, including the battery's 210 storage capacity, voltage, temperature and/or time under charge, among other examples.

The charging module 308 also includes charge status indicators 316 (e.g. colored light emitting diodes (LEDs)) associated with each of the battery connection interfaces 304. The charge status indicators present charge status information pertaining to the battery 210 connected to the battery connection interface 304 associated with the charge status indicator 316. In different examples, the charge status indicators 316 present the charge status information by emitting light of different colors, blinking, and/or based simply on an illumination state of the charge status indicators.

The interchangeable batteries 210 comprise battery connectors 302, which, in general facilitate connecting to and disconnecting from battery connection interfaces 304 of the wearable assembly 102 and/or of the charging device 306. This allows the batteries 210 to be easily swapped in and out, for example, between treatments administered using the body-mounted LIO system 100. The battery connectors 302 and the battery connection interfaces 304 include complementary attachment mechanisms for securing the battery 210 to the battery connection interface 304. In one example, the attachment mechanisms include complementary structural features of the battery connector 302 and battery connection interface 304 that guide the battery 210 to contact the battery connection interface 304 in a desired physical configuration (e.g. to ensure an electrical connection) and/or complementary clip mechanisms of the battery connector 302 and interface 304 for securing the battery 210 in place.

Similarly, the battery connector 302 and battery connection interface 304 include complementary electrical interfaces which provide an electrical connection between the battery 210 and the power module 110 or charging module 308.

Figure 10:
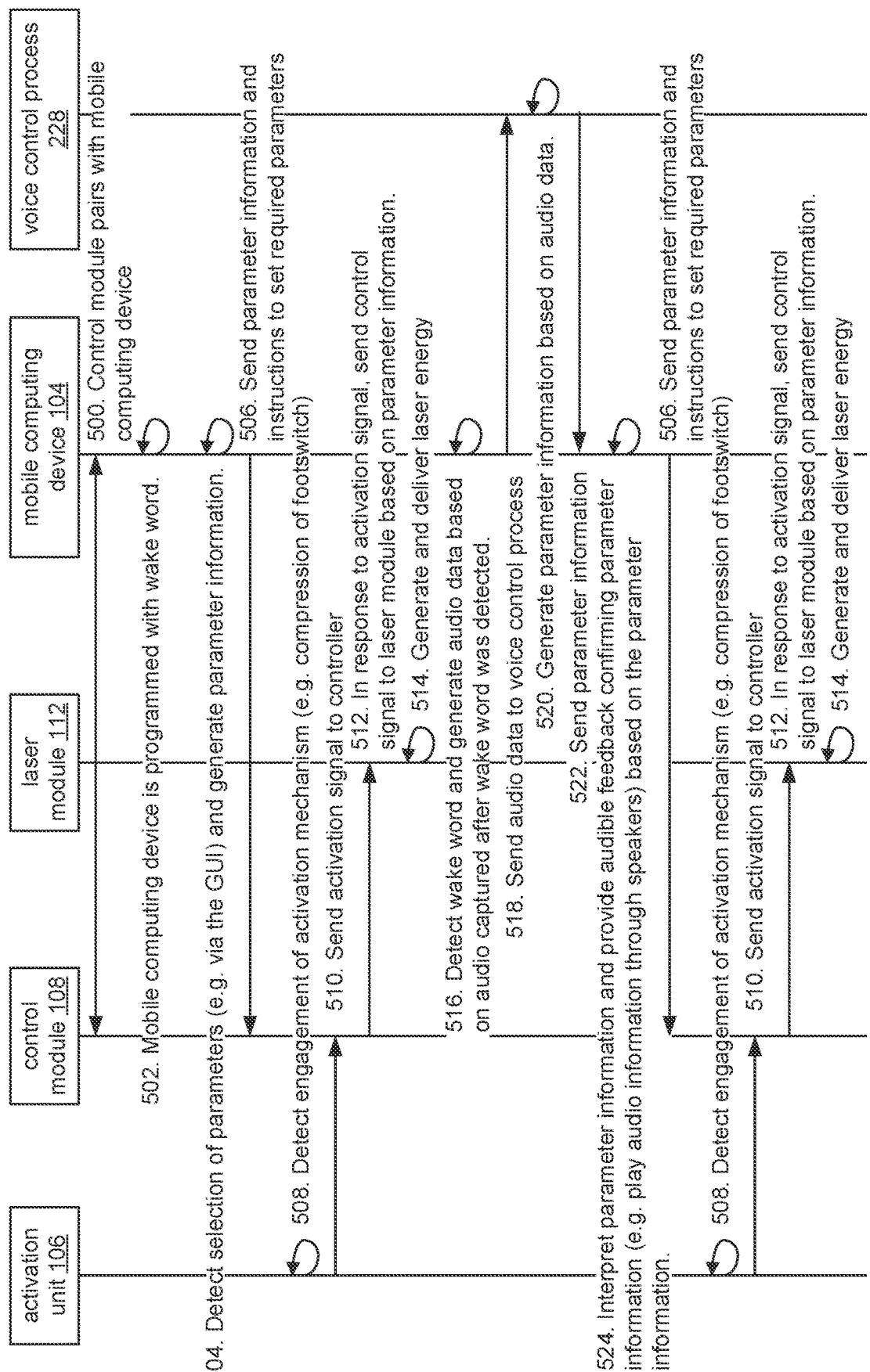
FIG. 10 is a sequence diagram illustrating a process by which the LIO system emits laser energy based on parameter information received via a graphical user interface and a voice control process.

FIG. 10 is a sequence diagram illustrating the process by which the LIO system 100 emits laser energy based on parameter information received via the GUI 232 and the voice control process 228.

First, in step 500, the control module 102 pairs with the mobile computing device 104 by, for example, establishing a wireless communication link and/or exchanging identification information for the two devices, among other examples.

In step 500, the mobile computing device 104 is then programmed with the wake word. The wake word can be programmed with a predetermined wake word upon manufacture or customized based on user input, for example.

In step 504, the mobile computing device 104 detects input via the GUI 232 or the UI in general and generates parameter information based on the input. In one example, the doctor selects a virtual button indicating the power parameter or enters via a virtual keyboard a numerical value indicating the desire power setting (e.g. 200). In another example, the doctor adjusts a dial or increment button indicating the desired power setting (e.g. 200).

In step 506, the mobile computing device 104 sends the parameter information to the control module 108 along with instructions to set the required parameters based on the parameter information, and the parameters are updated.

In step 508, the activation unit 106 detects engagement of the activation mechanism 245. In one example, the user's foot compresses a footswitch. In response, in step 510, the activation unit 106 sends an activation signal to the control module 108.

In response to receiving the activation signal, the control module 108 in step 512 sends a control signal to the laser module 112.

In step 514, in response to receiving the control signal, the laser module 112 generates and emits the laser energy according to the parameters set by the control module 108.

In step 516, the mobile computing device 104, which continuously and in real time monitors captured audio data for the wake word programmed in step 500, detects the wake word and, in response, generates audio data based on sound that was captured after the wake word was detected.

In step 518, the mobile computing device 104 sends the captured audio data to the voice control process 228.

In step 520, the voice control process 228 generates parameter information based on the audio data. In one example, the audio data includes spoken language such as the phrase "Power 200". The voice control process 228, for example via speech recognition processes, recognizes the phrase "Power 200" and translates the phrase into parameter information such as an attribute "power" with a value of "200". The voice control process 228 returns the generated parameter information in step 522.

In step 524, the mobile computing device 104, via the mobile application 226, interprets the parameter information, for example, by generating or retrieving audio data corresponding to the attributes and/or values indicated by the parameter information. The mobile computing device 104 then provides audible feedback confirming the parameter information for example by outputting sound through the speakers 236.

Steps 506 through 514 then proceed as previously described, as the control module 108 updates the parameters and the laser module 112 emits laser energy based on the updated parameters.

Figure 11:
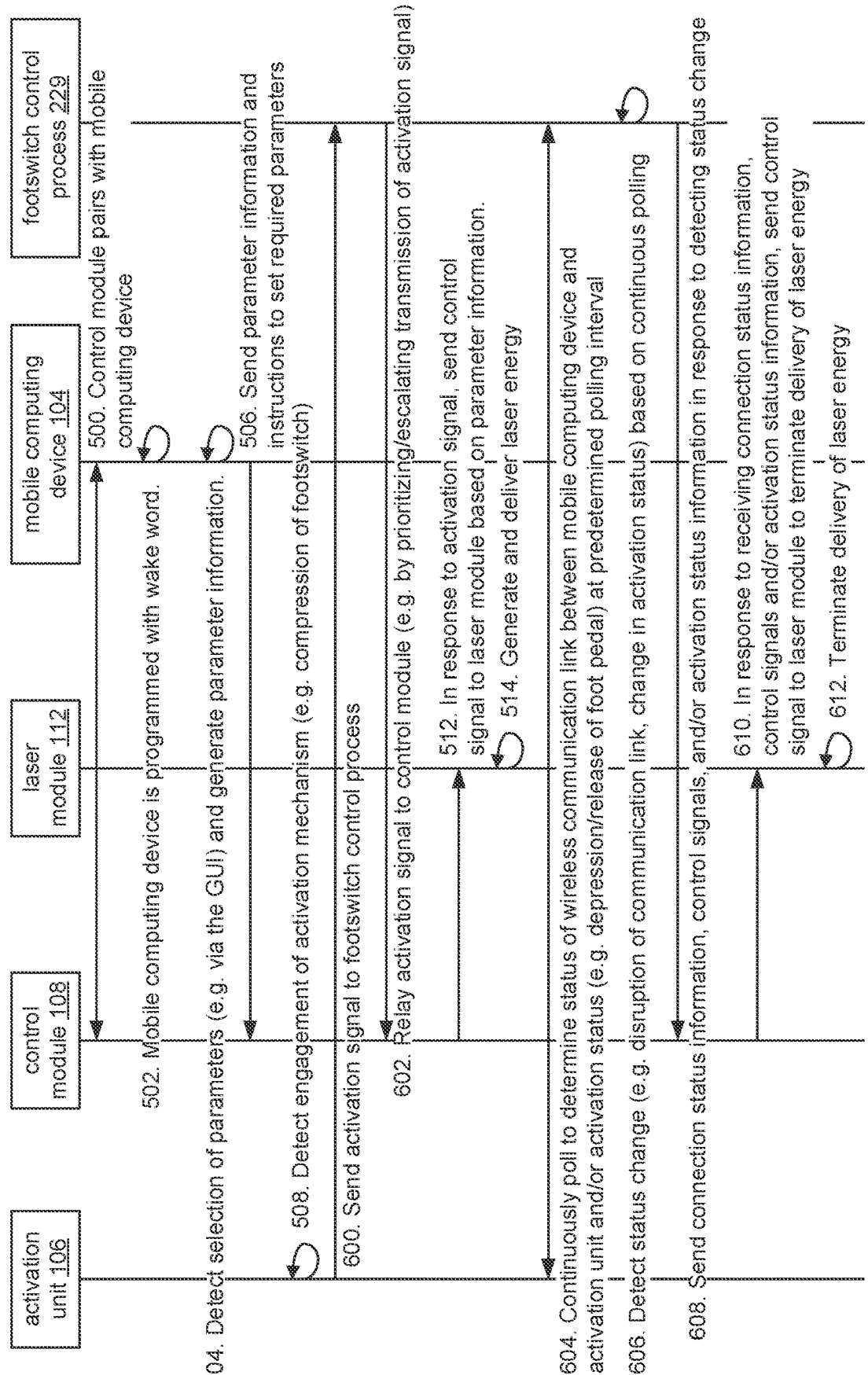
FIG. 11 is a sequence diagram illustrating a process by which the LIO system emits laser energy based on activation signals generated by a wireless activation unit controlled by a footswitch control process of a mobile computing device.

FIG. 11 is a sequence diagram illustrating the process by which the LIO system 100 emits laser energy based on activation signals, connection status information, control signals, and/or activation status information received from the footswitch control process 229 of the mobile computing device 104.

First, steps 500 through 508 proceed as previously described.

Now, however, in step 600, the activation unit 106 sends the activation signals to the footswitch control process 229 executing on the mobile computing device 104 via the devices' respective wireless interfaces 214, 220 and antennas 216, 218.

In step 602, in response to receiving the activation signal from the activation unit 106, the footswitch control process 229 relays the activation signal to the control module 108. In examples, the footswitch control process 229 receives and relays a discrete activation signal from the activation unit 106 to the control module 108, or the footswitch control process 229 receives and relays, on a continuous basis, a continuous activation signal from the activation unit 106 to the control module 108. The relayed activation signal is prioritized/escalated with respect to the other communication between the mobile computing device 104 and the control module 108 and/or with respect to computing functions of the CPU 222.

Steps 512 through 514 then proceed as previously described, as the control module 108 directs the laser module 112 to deliver the laser energy based on the activation signal.

In step 604, the footswitch control process 229 continuously polls the activation unit 106 to determine the status of the wireless communication link between the mobile computing device 104 and the activation unit 106 and/or the activation status of the activation unit 106 (e.g. whether a foot pedal of the activation unit 106 is depressed in an activated state or released in a neutral state). The footswitch control process 229 polls the activation unit 106, for example, by repetitively sending the query messages to the activation unit 106 in response to which the activation unit 106 returns response messages. The query messages (and thus the response messages) are transmitted at a frequency based on the predetermined polling interval.

In step 606, the footswitch control process 229 detects a status change based on the polling. In one example, the footswitch control process 229 detects a disruption of the wireless communication link between the mobile computing device 104 and the activation unit 106 by determining that an amount of elapsed time since receiving a response message from the activation unit 106 exceeds the predetermined threshold. In another example, the footswitch control process 229 detects a change in the activation status of the activation unit 106 based on activation status information included in the most recent response message.

In step 608, the footswitch control process 229 immediately sends connection status information, control signals, and/or activation status information to the control module 108 in response to detecting the status change. As in step 602, this transmission is prioritized/escalated with respect to the other communication between the mobile computing device 104 and the control module 108 and/or with respect to computing functions of the CPU 222 of the mobile computing device 104. In one example, the footswitch control process 229 sends the connection status information, indicating that the wireless communication link between the activation unit 106 and the mobile computing device 104 was disrupted, directly to the control module 108. In another example, the footswitch control process 229 sends control signals to the control module 108 indicating that the delivery of laser energy should be terminated. In another example, the footswitch control process 229 sends the activation status information indicating that the status changed from an activation status to a neutral status (e.g. the foot pedal of the activation unit 106, which was previously depressed, was released).

In step 610, based on the connection status information, control signals, and/or activation status information, the control module 108 causes the laser module 112 to stop delivery of laser energy (e.g. which was initiated in step 514) by sending control signals and/or by terminating transmission of the control signals to the laser module 112.

In step 612 the laser module 112 terminates delivery of the laser energy based on the control signals from the control module 108.

While this invention has been particularly shown and described with references to preferred embodiments thereof, it will be understood by those skilled in the art that various changes in form and details may be made therein without departing from the scope of the invention encompassed by the appended claims.

What is claimed is:

1. A laser indirect ophthalmoscope system for delivering laser energy to an eye of a patient, the system comprising:
 a voice control process for receiving audio data captured from a mobile computing device and generating parameter information based on the captured audio data, the voice control process executing on the mobile computing device;

a laser module for generating and delivering the laser energy to the eye;

a wearable assembly for securing the laser module to a body of a user of the laser indirect ophthalmoscope system; and a control module for receiving the parameter information and setting parameters from the mobile computing device for the delivered laser energy based on the parameter information, the control module being housed within a housing remote from the mobile computing device.

2. The system as claimed in claim 1, wherein the voice control process generates the parameter information by recognizing spoken language in the captured audio data.

3. The system as claimed in claim 1, wherein the audio data is captured in response to detecting a predetermined wake word.

4. The system as claimed in claim 1, wherein audible feedback is provided by the mobile computing device confirming the parameter information.

5. The system as claimed in claim 1, wherein the parameter information received from the mobile computing device is further based on input received via a graphical user interface rendered on a touchscreen display of the mobile computing device.

6. The system as claimed in claim 1, wherein the parameter information received from the mobile computing device is further based on input received via one or more peripheral devices.

7. The system as claimed in claim 1, further comprising an activation unit for sending activation signals for emitting the laser energy to the control module in response to engagement of an activation mechanism of the activation unit.

8. The system as claimed in claim 7, wherein the activation unit is a footswitch, and the activation mechanism includes compression of the footswitch.

9. The system as claimed in claim 1, wherein the control module comprises a wireless communication interface for receiving the parameter information from the mobile computing device.

10. The system as claimed in claim 1, wherein the wearable assembly includes at least a headset worn on the user's head.

11. The system as claimed in claim 1, wherein the wearable assembly includes at least a utility belt worn around the user's waist.

12. The system as claimed in claim 1, wherein the wearable assembly secures the control module to the body of the user.

13. The system as claimed in claim 1, wherein the wearable assembly secures a power module for providing power to the laser module.

14. The system as claimed in claim 13, wherein the power module comprises a portable battery for providing the power.

15. The system as claimed in claim 14, further comprising a footswitch unit for sending activation signals for emitting the laser energy to the control module in response to compression of the footswitch unit, wherein the portable battery is in the footswitch unit.

* * * * *